(12) United States Patent
Kawaguchiya et al.

(10) Patent No.: US 8,716,681 B1
(45) Date of Patent: May 6, 2014

(54) SAMPLE PROCESSING METHOD

(71) Applicant: Kabushiki Kaisha Toshiba, Tokyo (JP)

(72) Inventors: Hitomi Kawaguchiya, Yokohama (JP);
Mitsuo Koike, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 14/015,957

(22) Filed: Aug. 30, 2013

(30) Foreign Application Priority Data

Feb. 13, 2013 (JP) ................. 2013-025579

(51) Int. Cl.
*A61N 5/00* (2006.01)
*G21G 5/00* (2006.01)
(52) U.S. Cl.
USPC ........... 250/492.1; 250/492.2; 250/492.21; 250/309; 250/310; 250/311; 250/307; 250/423 R; 250/423 F; 250/424; 250/426
(58) Field of Classification Search
USPC ........... 250/492.1, 492.21, 492.2, 309–311, 250/307, 432 R, 423 F, 424, 426
See application file for complete search history.

(56) References Cited

U.S. PATENT DOCUMENTS

| | | | |
|---|---|---|---|
| 6,527,967 B1 | 3/2003 | Suzuki | |
| 6,664,552 B2 * | 12/2003 | Shichi et al. | 250/492.21 |
| 7,002,150 B2 | 2/2006 | Iwasaki et al. | |
| 8,274,049 B2 * | 9/2012 | Tanaka et al. | 250/311 |
| 8,610,060 B2 * | 12/2013 | Asai et al. | 250/311 |

FOREIGN PATENT DOCUMENTS

JP 2006-164792 A 6/2006

* cited by examiner

*Primary Examiner* — Jack Berman
*Assistant Examiner* — Meenakshi Sahu
(74) *Attorney, Agent, or Firm* — Holtz, Holtz, Goodman & Chick, PC

(57) ABSTRACT

In one embodiment, a sample processing method includes placing a sample on a sample placing module, and setting first processing boxes on one side of slice formation scheduled regions of the sample, and second processing boxes on the other side thereof. The method includes processing the sample by performing a primary scan which sequentially scans the first processing boxes with a continuously generated ion beam, and a secondary scan which sequentially scans the second processing boxes with a continuously generated ion beam, to form slices of the sample. The primary and secondary scans are performed so that a first scanning condition for scanning first regions within the first and second processing boxes is set different from a second scanning condition for scanning second regions between the first processing boxes and between the second processing boxes, to allow frame portions of the sample to remain in the second regions.

20 Claims, 10 Drawing Sheets

SAMPLE PROCESSING METHOD

CROSS REFERENCE TO RELATED APPLICATION

This application is based upon and claims the benefit of priority from the prior Japanese Patent Application No. 2013-025579, filed on Feb. 13, 2013, the entire contents of which are incorporated herein by reference.

FIELD

Embodiments described herein relate to a sample processing method.

BACKGROUND

When a sample for an electron microscope is processed by a focused ion beam (FIB) apparatus, the sample is processed with a focused ion beam to fabricate an observation slice. In this case, if plural slices are individually fabricated, final thicknesses of these slices are varied because it is difficult to uniform conditions for processing the slices.

DETAILED DESCRIPTION

Embodiments will now be explained with reference to the accompanying drawings.

In one embodiment, a sample processing method includes placing a sample on a sample placing module. The method further includes setting first processing boxes on one side of slice formation scheduled regions of the sample, and setting second processing boxes on the other side of the slice formation scheduled regions of the sample. The method further includes processing the sample by performing a primary scan which sequentially scans the first processing boxes with a continuously generated ion beam, and a secondary scan which sequentially scans the second processing boxes with a continuously generated ion beam, to form a plurality of slices of the sample. The primary and secondary scans are performed so that a first scanning condition for scanning first regions within the first and second processing boxes is set different from a second scanning condition for scanning second regions between the first processing boxes and between the second processing boxes, to allow frame portions of the sample to remain in the second regions after the slices are formed.

First Embodiment

FIGS. 1A to 1D are perspective views and a top view for explaining a sample processing method of a first embodiment.

Figure 1A:
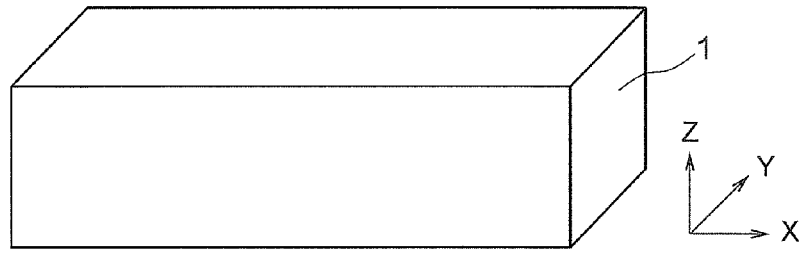
FIGS. 1A to 1D are perspective views and a top view for explaining a sample processing method of a first embodiment.

FIG. 1A is a perspective view showing a sample 1 before slices are formed. The sample 1 of FIG. 1A is a block cut away from a semiconductor wafer.

Figure 10:
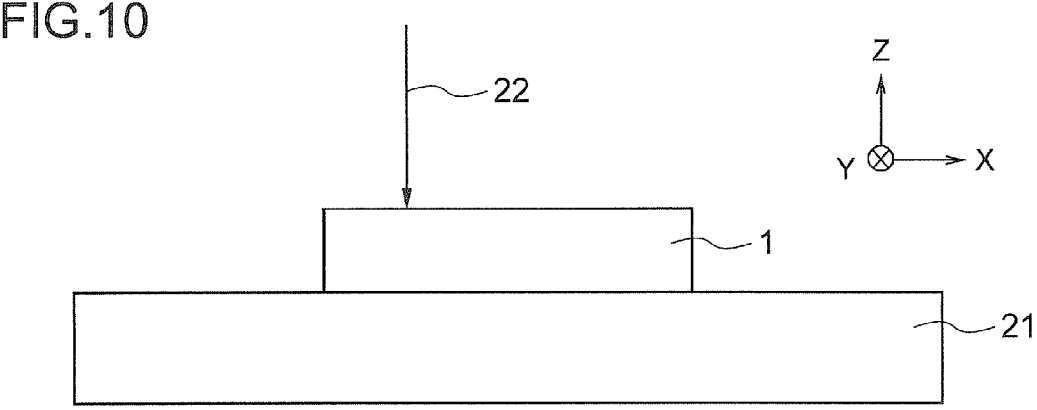
FIG. 10 is a cross-sectional view schematically showing a sample of the first embodiment irradiated with a focused ion beam.

The sample 1 is placed on a sample placing module 21 and is processed with a focused ion beam 22 as shown in FIG. 10. FIG. 10 is a cross-sectional view schematically showing the sample 1 of the first embodiment irradiated with the focused ion beam 22. The X and Y directions respectively represent directions parallel to an upper surface of the sample 1 and vertical to each other. The Z direction represents a direction vertical to the upper surface of the sample 1. Examples of the sample placing module 21 include a holder, a stage and a shuttle.

Figure 1B:
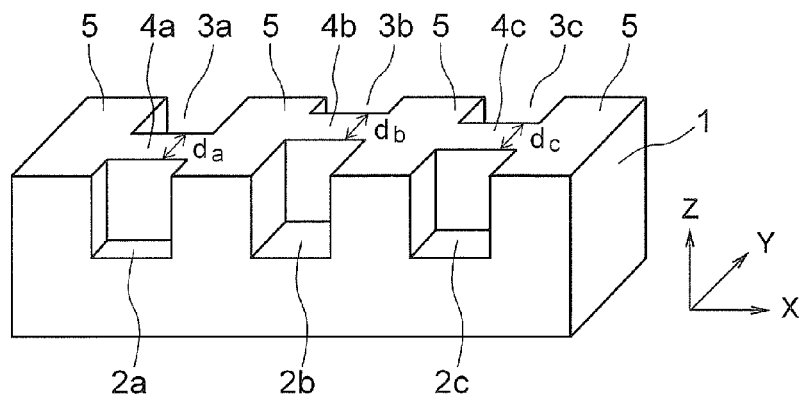

FIG. 1B is a perspective view showing the sample 1 in which plural slices 4a to 4c are formed. In this method, first openings 2a to 2c and second openings 3a to 3c are formed in the sample 1 by the focused ion beam 22, so that the slices 4a to 4c are formed between the first openings 2a to 2c and the second openings 3a to 3c.

Reference characters "$d_a$" to "$d_c$" in FIG. 1B designate thicknesses of the slices 4a to 4c, respectively. Reference numeral 5 designates frame portions remaining on both ends of the slices 4a to 4c, the first openings 2a to 2c and the second openings 3a to 3c after the slices 4a to 4c are completed. The frame portions 5 have a function of reinforcing the strength of the slices 4a to 4c.

Figure 1C:
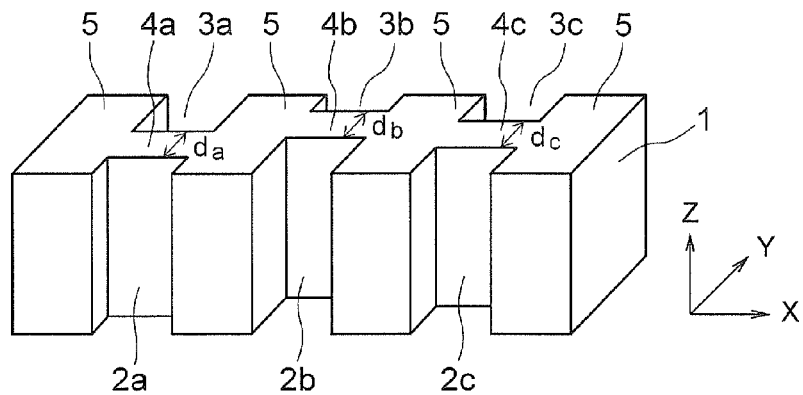

Although the first and second openings 2a to 3c do not penetrate the sample 1 in FIG. 1B, they may penetrate the sample 1 as shown in FIG. 1C. Although the positions of the slices 4a to 4c are shifted from each other in the Y direction in FIGS. 1B and 1C, it is not necessarily needed to shift these positions from each other in the Y direction.

Figure 1D:
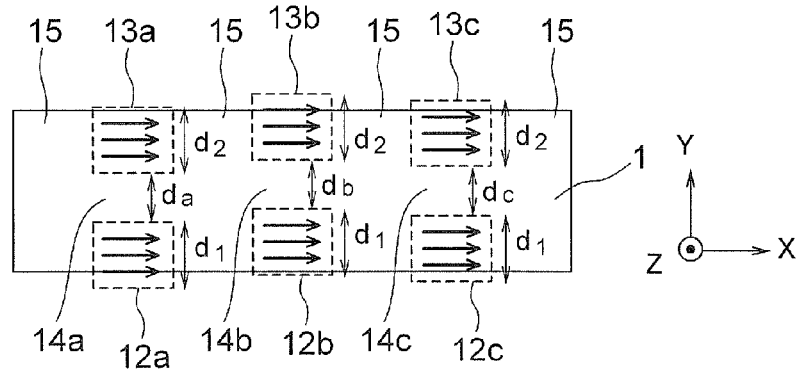

FIG. 1D is a top view showing a method of forming the slices 4a to 4c. This method forms the sample 1 of FIG. 1B or 1C from the sample 1 of FIG. 1A.

First, first processing boxes 12a to 12c are set on one side of slice formation scheduled regions 14a to 14c of the sample 1, and second processing boxes 13a to 13c are set on the other side of the slice formation scheduled regions 14a to 14c of the sample 1. The slice formation scheduled regions 14a to 14c are regions scheduled to form the slices 4a to 4c in the sample 1. The first and second processing boxes 12a to 13c are virtual boxes which are set in regions scheduled to form the first and second openings 2a to 3c in the sample 1 by software which controls an FIB apparatus. Reference characters "$d_1$" and "$d_2$" respectively designate widths of the first and second processing boxes 12a to 13c in the Y direction (thickness direction of the slices 4a to 4c). Reference numeral 15 designates frame formation scheduled regions of the sample 1, which are regions to form the frames 5 in the sample 1.

Next, regions within the first and second processing boxes 12a to 13c are scanned by the focused ion beam and are sputter-etched to form the first and second openings 2a to 3c. As a result, the slices 4a to 4c are formed in the slice formation scheduled regions 14a to 14c. In the frame formation scheduled regions 15, the frame portions 5 are made to remain.

Hereinafter, a detailed description is given of the sample processing method of FIG. 1D with reference to FIGS. 2A to 2C.

Figure 2A:
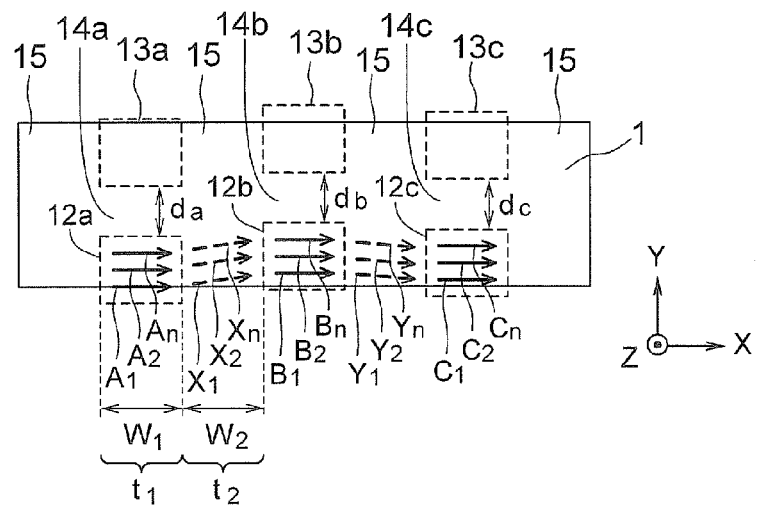
FIGS. 2A to 2C are top views for explaining the sample processing method of the first embodiment in detail.
Figure 2B:
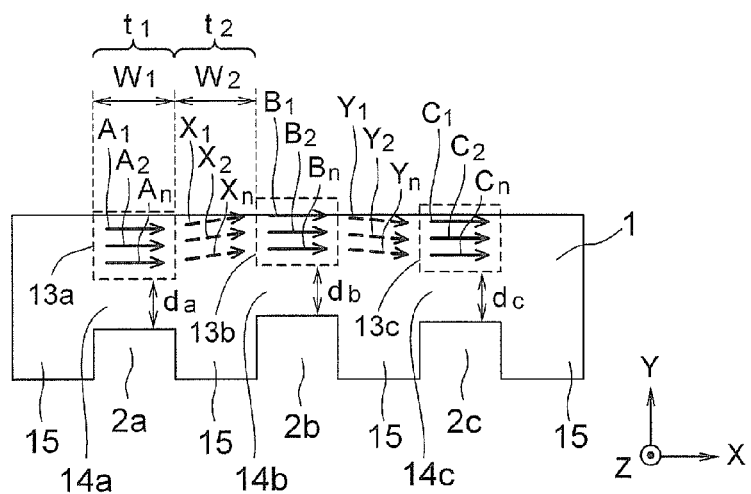
Figure 2C:
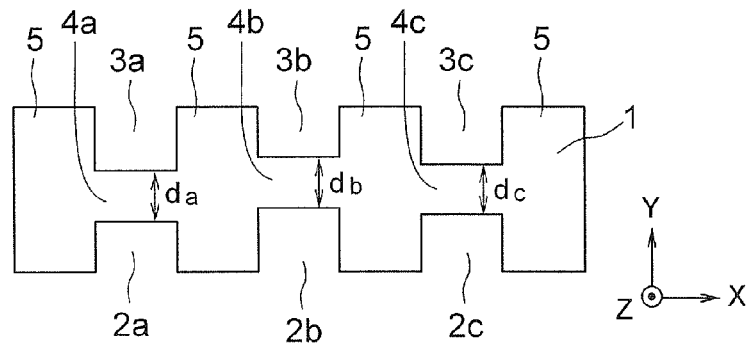

FIGS. 2A to 2C are top views for explaining the sample processing method of the first embodiment in detail.

First, as shown in FIG. 2A, primary scans are performed a plurality of times, where each primary scan sequentially scans the first processing boxes 12a to 12c with a continuously generated focused ion beam once. As a result, the first openings 2a to 2c are formed in the sample 1 (FIG. 2B).

Next, as shown in FIG. 2B, secondary scans are performed a plurality of times, where each secondary scan sequentially scans the second processing boxes 13a to 13c with a continuously generated focused ion beam once. As a result, the second openings 3a to 3c are formed in the sample 1 (FIG. 2C).

In this way, the slices 4a to 4c are formed in the sample 1 as shown in FIG. 2C.

Reference character "$W_1$" designates a length of the first and second processing boxes 12a to 13c in the X direction. In the present embodiment, the length "$W_1$" takes the same value in these processing boxes 12a to 13c.

Reference character "$W_2$" designates a length of the frame formation scheduled regions 15 between the first processing boxes 12a to 12c and between the second processing boxes 13a to 13c in the X direction. In the present embodiment, the length "$W_2$" takes almost the same value in these frame formation scheduled regions 15. For example, the length "$W_2$" is about 1 μm. In the present embodiment, the length "$W_1$" and the length "$W_2$" are set at almost the same length.

In the present embodiment, the width "$d_1$" (see FIG. 1) of the first processing boxes 12a to 12c in the Y direction takes the same value in these processing boxes 12a to 12c, and the width "$d_2$" of the second processing boxes 13a to 13c in the Y direction also takes the same value in these processing boxes 13a to 13c. In the present embodiment, the widths "$d_1$" and "$d_2$" are set at almost the same width.

Hereinafter, regions within the first and second processing boxes 12a to 13c are referred to as "first regions" and regions between the first processing boxes 12a to 12c and between the second processing boxes 13a to 13c are referred to as "second regions."

Reference character "$t_1$" designates first dwell time for scanning each first region within the first and second processing boxes 12a to 13c. In the present embodiment, the first dwell time "$t_1$" takes the same value in the first regions of the sample 1.

Reference character "$t_2$" designates second dwell time for scanning each second region between the first processing boxes 12a to 12c and between the second processing boxes 13a to 13c. In the present embodiment, the second dwell time "$t_2$" takes the same value in the second regions of the sample 1.

Hereinafter, a detailed description is given of the primary scans which scan the first processing boxes 12a to 12c with reference to FIG. 2A. Since the secondary scans which scan the second processing boxes 13a to 13c are performed in a similar manner to the primary scans, a detailed description about the secondary scans is omitted.

In a first primary scan, a first region within the first processing box 12a is scanned in the first dwell time "$t_1$" as shown with arrow "$A_1$". Next, as shown with arrow "$X_1$", a second region between the first processing boxes 12a and 12b is scanned in the second dwell time "$t_2$". Next, as shown with arrow "$B_1$", a first region within the first processing box 12b is scanned in the first dwell time "$t_1$". Next, as shown with arrow "$Y_1$", a second region between the first processing boxes 12b and 12c is scanned in the second dwell time "$t_2$". Next, as shown with arrow "$C_1$", a first region within the first processing box 12c is scanned in the first dwell time "$t_1$". In this way, the first primary scan is finished.

The second and subsequent primary scans are executed in a similar manner to the first primary scan. The second primary scan is performed in order of arrows "$A_2$", "$X_2$", "$B_2$", "$Y_2$" and "$C_2$". The n-th (n is an integer of 3 or larger) primary scan is performed in order of arrow "$A_n$", "$X_n$", "$B_n$", "$Y_n$", and "$C_n$". In this way, the first openings 2a to 2c are formed.

In the present embodiment, each primary scan is performed with a continuously generated ion beam. For example, the first primary scan is performed while an ion beam is generated from arrow "$A_1$" to arrow "$C_1$". This makes it possible to execute a scan from arrow "$A_1$" to arrow "$C_1$" without changing parameters such as intensity, an acceleration voltage, and beam current of the ion beam. Similarly, the n-th primary scan is performed while an ion beam is generated from arrow "$A_n$" to arrow "$C_n$".

As described above, each primary scan of the present embodiment is performed so that the first processing boxes 12a to 12c are sequentially scanned with a continuously generated ion beam. Similarly, each secondary scan of the present embodiment is performed so that the second processing boxes 13a to 13c are sequentially scanned with a continuously generated ion beam.

Therefore, in the present embodiment, it is possible to execute each of the primary and secondary scans without changing parameters such as intensity, an acceleration voltage, and beam current of the ion beam, so that occurrence of variations in thicknesses "$d_a$" to "$d_c$" of the slices 4a to 4c can be suppressed. Making the thicknesses "$d_a$" to "$d_c$" of the slices 4a to 4c to be uniform brings about such an advantage as facilitating quantitative comparison between observation results of the slices 4a to 4c.

However, in the present embodiment, since the first and second processing boxes 12a to 13c are sequentially scanned with a continuously generated ion beam, not only the first regions within the first and second processing boxes 12a to 13c but also the second regions between the processing boxes 12a to 12c and between the second processing boxes 13a to 13c are etched. In this case, if the frame portions 5 between the first processing boxes 12a to 12c and between the second processing boxes 13a to 13c disappears, the slices 4a to 4c may be twisted, which may hinder appropriate observation.

Accordingly, in the present embodiment, to cope with the disappearance of the frame portions 5, a first scanning condition for scanning the first regions within the first and second processing boxes 12a to 13c are set different from a second scanning condition for scanning the second regions between the first processing boxes 12a to 12c and between the second processing boxes 13a to 13c.

More specifically, the second dwell time "$t_2$" is set shorter than the first dwell time "$t_1$" ($t_2<t_1$) in the primary and secondary scans. In other words, the first regions within the first and second processing boxes 12a to 13c are slowly scanned, while the second regions between the first processing boxes 12a to 12c and between the second processing boxes 13a to 13c are quickly scanned in the present embodiment.

As a result, an etching amount in the second regions between the first processing boxes 12a to 12c and between the second processing boxes 13a to 13c becomes smaller than an etching amount in the first regions within the first and second processing boxes 12a to 13c. Therefore, according to the present embodiment, it is possible to allow the frame portions 5 to remain in the second regions between the first processing boxes 12a to 12c and between the second processing boxes 13a to 13c after the slices 4a to 4c are formed.

In the present embodiment, it is preferable to set the second dwell time "$t_2$" to be 1/1000 or less of the first dwell time "$t_1$" ($t_2 \leq t_1/1000$). For example, when the first dwell time "$t_1$" is 10μ second, the second dwell time "$t_2$" is preferably set to 0.01μ, second or less. The reason why such setting is preferable will be described in detail with reference to FIGS. 3A to 5C.

(1) Explanation of FIGS. 3A to 5C

FIGS. 3A to 5C are cross-sectional views regarding the sample processing method of the first embodiment in the cases of $t_2=t_1/10$, $t_2=t_1/100$, and $t_2=t_1/1000$, respectively. Reference character "H" designates a height of the slices 4a to 4c (=a depth of the openings 2a to 3c).

Figure 3A:
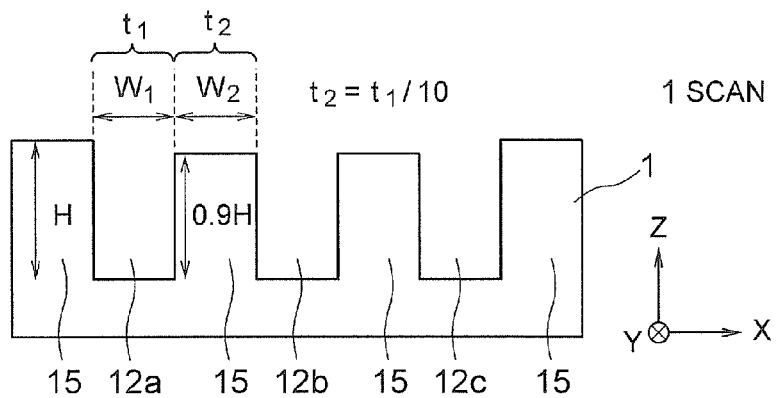
FIGS. 3A to 3C are cross-sectional views regarding the sample processing method of the first embodiment in a case of $t_2 = t_1/10$.

FIG. 3A shows a cross-section of the sample 1 at the time when the first primary scan has been finished in the case of $t_2=t_1/10$. As shown in FIG. 3A, holes with a depth "H" are formed in the first regions within the first processing boxes 12a to 12c which were scanned by an ion beam. These holes are to be formed into the openings 2a to 2c in the end. The height of the frame formation scheduled regions 15 is reduced to 0.9H. This value is approximately estimated on the basis that "$t_2$" is 1/10 of "$t_1$" and therefore an etching rate of the frame formation scheduled regions 15 is 1/10 of an etching rate of the processing boxes 12a to 12c.

Figure 3B:
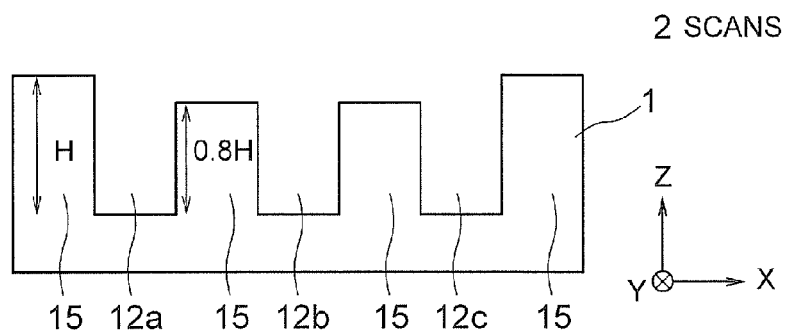
Figure 3C:
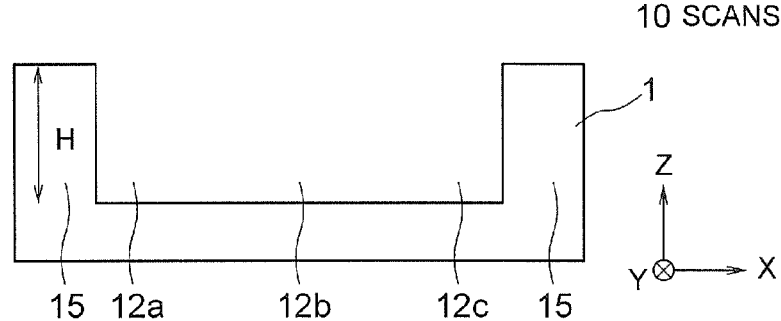

FIGS. 3B and 3C respectively show cross-sections of the sample 1 at the time when the second and tenth primary scans have been finished in the case of $t_2=t_1/10$. As shown in FIG. 3C, in the case of $t_2=t_1/10$, the height of the frame formation scheduled regions 15 disappears after execution of ten scans. In this case, the slices 4a to 4c may be twisted.

Figure 4A:
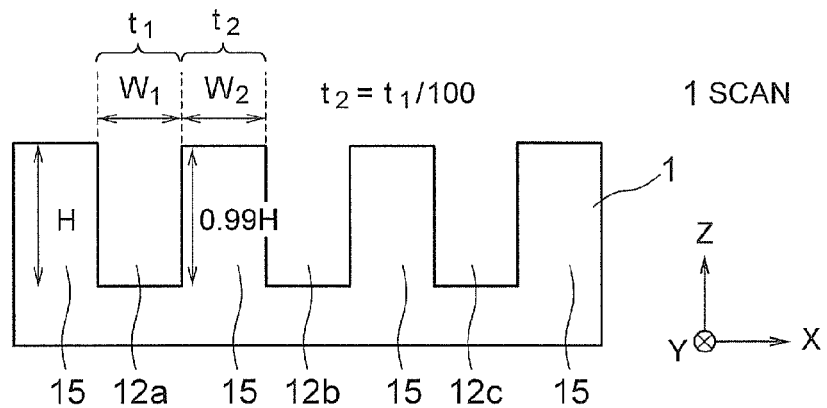
FIGS. 4A to 4C are cross-sectional views regarding the sample processing method of the first embodiment in a case of $t_2 = t_1/100$.
Figure 4B:
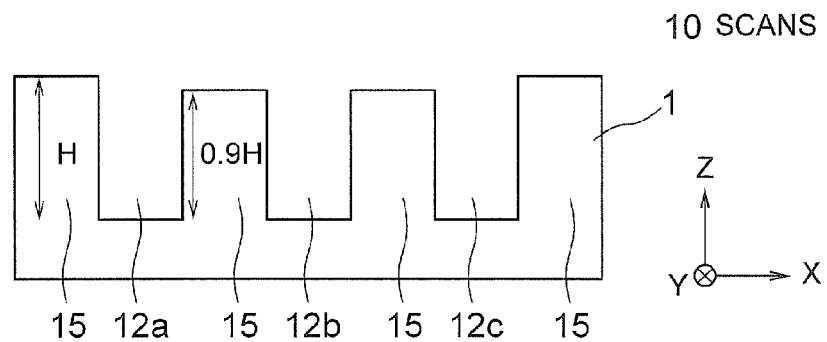
Figure 4C:
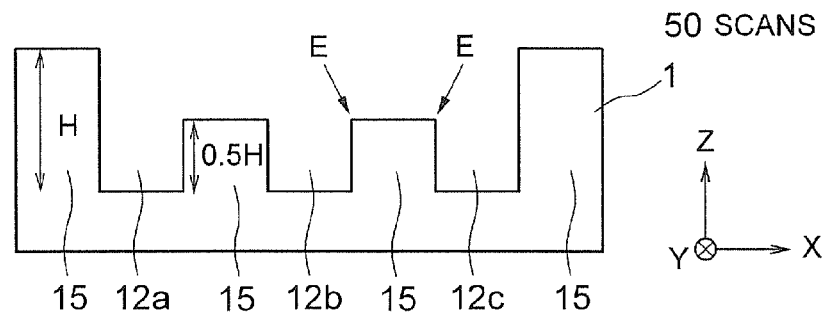

FIGS. 4A and 4C respectively show cross-sections of the sample 1 at the time when the first, tenth, and fiftieth primary scans have been finished in the case of $t_2=t_1/100$. In the case of $t_2=t_1/100$, the etching rate of the frame formation scheduled regions 15 is slowed as compared with the case of $t_2=t_1/10$. However, the height of the frame formation scheduled regions 15 is reduced up to 0.5H at the time when 50 scans have been performed as shown in FIG. 4C.

Generally, the processing boxes 12a to 12c are scanned with an ion beam about a few dozen times to a few hundred times until the slices 4a to 4c are completed. In order to sufficiently reinforce the strength of the slices 4a to 4c, the height of the frame portions is preferably equal to or more than half of the height "H" of the slices 4a to 4c. However, in the case of $t_2=t_1/100$, the height of the frame formation scheduled regions 15 is reduced up to 0.5H by execution of 50 scans, and therefore there is a possibility that the strength of the slices 4a to 4c cannot sufficiently be reinforced.

Figure 5A:
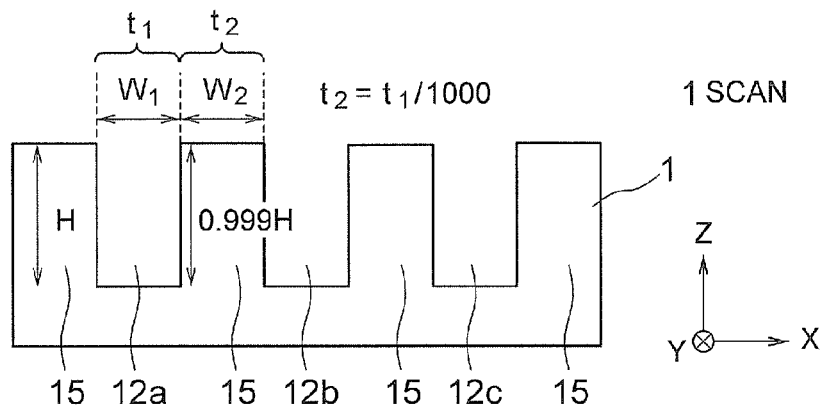
FIGS. 5A to 5C are cross-sectional views regarding the sample processing method of the first embodiment in a case of $t_2 = t_1/1000$.
Figure 5B:
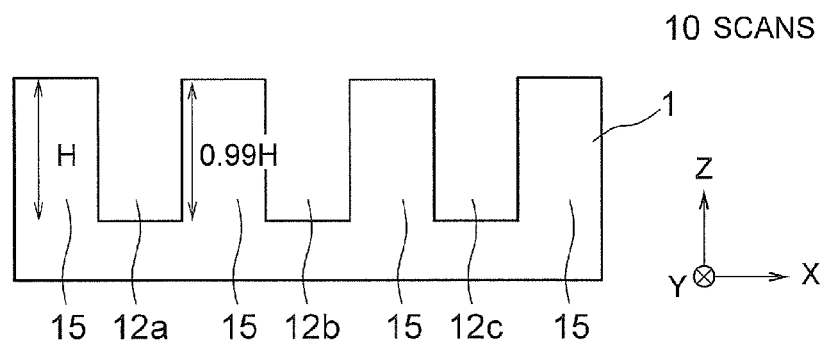
Figure 5C:
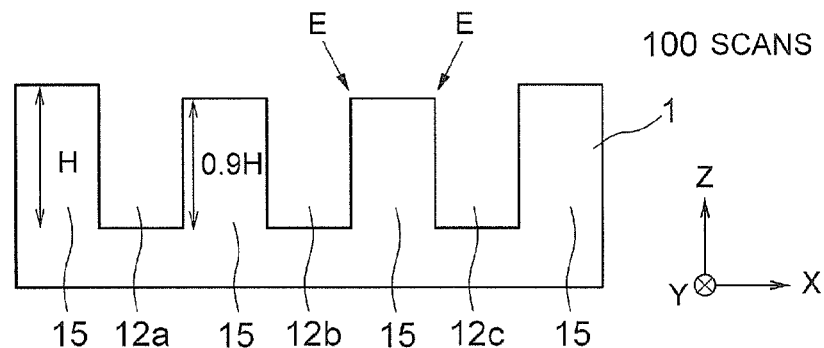

FIGS. 5A and 5C respectively show cross-sections of the sample 1 at the time when the first, tenth, and hundredth primary scans have been finished in the case of $t_2=t_1/1000$. As shown in FIG. 5A, in the case of $t_2=t_1/1000$, the height of the frame formation scheduled regions 15 is kept at 0.9 H even after execution of 100 scans. Therefore, in the case of $t_2=t_1/1000$, it can be considered that the height of the frame portions 5 is sufficiently secured even after execution of about several hundred scans and the strength of the slices 4a to 4c can sufficiently be reinforced.

Therefore, it is preferable to set the second dwell time "$t_2$" to be 1/1000 or less of the first dwell time "$t_1$" in the present embodiment.

Reference character "E" in FIGS. 4C and 5C designates edge portions of the frame formation scheduled regions 15. Since the etching rate in the edge portions "E" is larger than that in other portions, repeated scanning with an ion beam causes the edge portions "E" to be rounded. As a consequence, an effective height of the frame formation scheduled regions 15 is lowered, which may possibly hinder sufficient reinforcement of the strength of the slices 4a to 4c.

Accordingly, the first and second dwell time "$t_1$" and "$t_2$" are preferably set in consideration of the rounding of the edge portions "E". Moreover, since increasing the length "$W_2$" in the X direction of the frame formation scheduled regions 15 weakens an influence of rounding of the edge portions "E", it is preferable to set the length "$W_2$" to be long enough to successfully avoid the influence of rounding of the edge portions "E".

(2) Modification of First Embodiment

A modification of the first embodiment will be described with reference to FIGS. 2A to 2C again.

In FIGS. 2A and 2B, after all the primary scans are finished and the first openings 2a to 2c are completed, the secondary scans are started to fabricate the second openings 3a to 3c. However, in the present embodiment, the primary and secondary scans may be performed alternately in the order of, for example, the first primary scan, the first secondary scan, the second primary scan, and the second secondary scan. In this case, the primary and second scans may be performed alternately in the order of a primary scan, a secondary scan, a primary scan, and a secondary scan as described above, or may be performed alternately in the order of primary scans, secondary scans, primary scans, and secondary scans.

In FIGS. 2A and 2B, the primary and secondary scans are both performed so as to proceed in +X direction only. However, in the present embodiment, at least in one of the primary and secondary scans, both a +X directional scan which proceeds in +X direction and a −X directional scan which proceeds in −X direction may be performed. For example, odd-numbered scans such as scans "$A_1$" to "$C_1$" may be performed so as to proceed in +X direction, while even-numbered scans such as scans "$A_2$" to "$C_2$" may be performed so as to proceed in −X direction.

Moreover, the primary and secondary scans in the present embodiment are performed so that the second dwell time "$t_2$" is set shorter than the first dwell time "$t_1$". In other words, the first regions within the first and second processing boxes 12a to 13c are slowly scanned, while the second regions between the first processing boxes 12a to 12c and between the second processing boxes 13a to 13c are quickly scanned in the primary and secondary scans in the present embodiment. The second dwell time "$t_2$" is preferably set to 1/1000 or less of the first dwell time "$t_1$".

As described in the explanation of FIGS. 3A to 5C, a ratio between the etching rate in the first regions and the etching rate in the second regions generally coincides with a ratio between the first dwell time "$t_1$" and the second dwell time "$t_2$".

However, the ratio between these etching rates also depends on a ratio between a first ion beam scanning distance (=length "$W_1$") in the first dwell time "$t_1$" and a second ion beam scanning distance (=length "$W_2$") in the second dwell time "$t_2$". This is because a longer scanning distance in a fixed time tends to shorten a period of time for irradiating the same portion with an ion beam and to slower the etching rate.

Accordingly, a relationship between the scans of the first regions and the scans of the second regions may be defined with a scanning speed instead of dwell time in the present embodiment. The scanning speed is obtained by dividing an ion beam scanning distance by dwell time.

More specifically, the relationship can be defined by using a first scanning speed "$V_1$" for scanning each first region within the first and second processing boxes 12a to 13c, and a second scanning speed "$V_2$" for scanning each second region between the first processing boxes 12a to 12c and between the second processing boxes 13a to 13c.

For example, the primary and secondary scans of the present embodiment may be performed so that the second scanning speed "$V_2$" is set faster than the first scanning speed "$V_1$." ($V_2 > V_1$). The reason of this setting is similar to the reason why $t_2 < t_1$ is set. The second scanning speed "$V_2$" is preferably set to be 1000 times or more of the first scanning speed "$V_1$" ($V_2 \geq V_1 \times 1000$). The reason of this setting is also similar to the reason why $t_2 \leq t_1/1000$ is preferable.

As described above, each of the primary and secondary scans of the present embodiment is performed so that the first or second processing boxes 12a to 13c are sequentially scanned with a continuously generated ion beam. Therefore, according to the present embodiment, it is possible to suppress occurrence of variations in thicknesses of the slices 4a to 4c.

Moreover, in the present embodiment, the first scanning condition for scanning the first regions within the first and second processing boxes 12a to 13c are made different from the second scanning condition for scanning the second regions between the first processing boxes 12a to 12c and between the second processing boxes 13a to 13c, to allow the frame portions 5 to remain in the second regions after the slices 4a to 4c are formed. Therefore, according to the present embodiment, it is possible to suppress occurrence of variations in thicknesses of the slices 4a to 4c while reinforcing the strength of the slices 4a to 4c with the presence of the frame portions 5.

Second Embodiment

FIGS. 6A to 6D are perspective views and a top view for explaining a sample processing method of a second embodiment.

Figure 6A:
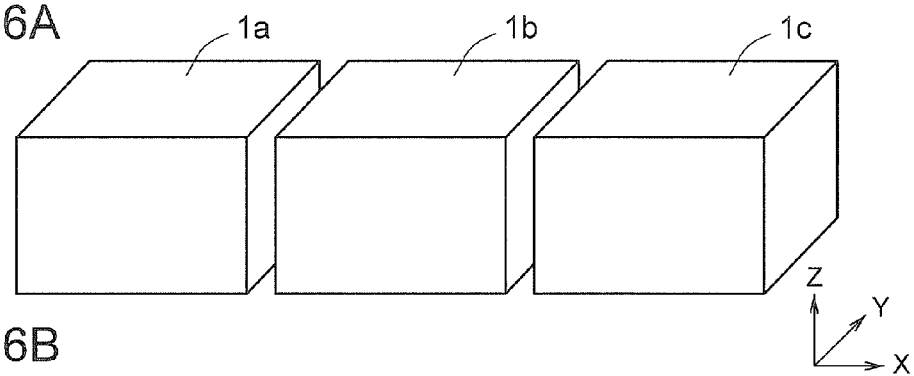
FIGS. 6A to 6D are perspective views and a top view for explaining a sample processing method of a second embodiment.

FIG. 6A is a perspective view showing plural samples 1a to is before slices are formed. These samples is to is are picked up by a lift-out technique and then are placed in alignment on a grid which is fixed to the sample placing module 21 (see FIG. 10). The samples is to is have almost the same height and are placed in the vicinity of each other in the same visual field. The samples is to is are processed with the focused ion beam 22 (see FIG. 10).

Figure 11A:
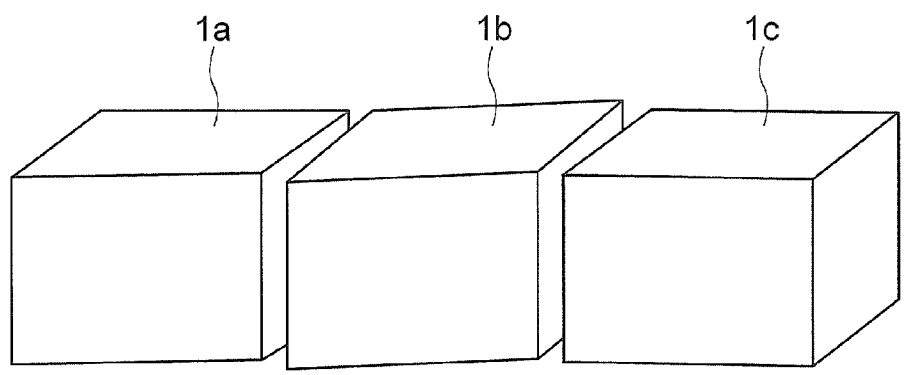
FIGS. 11A and 11B are a perspective view and a top view showing an example of placed samples of the second embodiment.
Figure 11B:
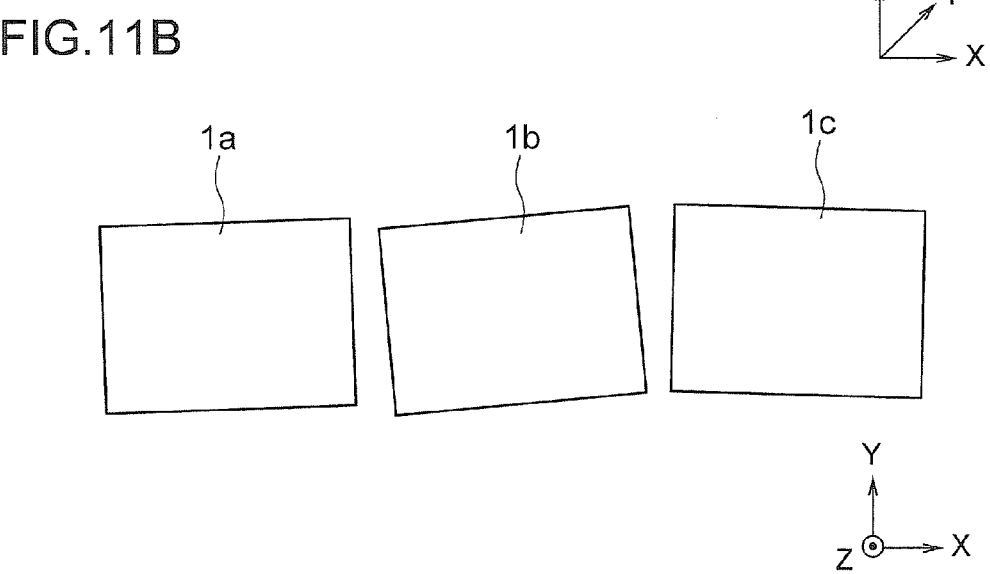

The samples 1a to 1c are preferably placed in alignment as much as possible by using device structure inside the samples is to 1c, crystal planes of the samples 1a to 1c or the like. FIGS. 11A and 11B are a perspective view and a top view showing an example of the placed samples 1a to is of the second embodiment.

FIGS. 11A and 11B show the samples is to 1c placed with a slight inclination with respect to each other due to an error at the time of placement. It is preferable that inclination of these samples 1a to is be corrected by using their device structure or crystal planes so that the samples is to is are aligned as much as possible according to purposes.

Figure 6B:
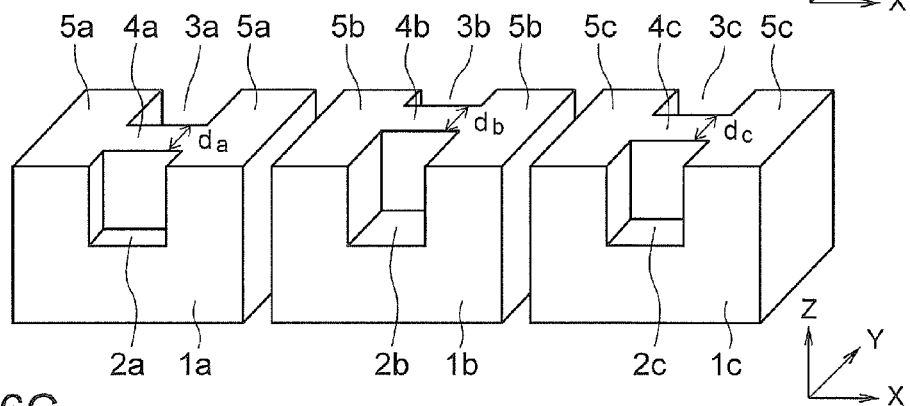
Figure 6C:
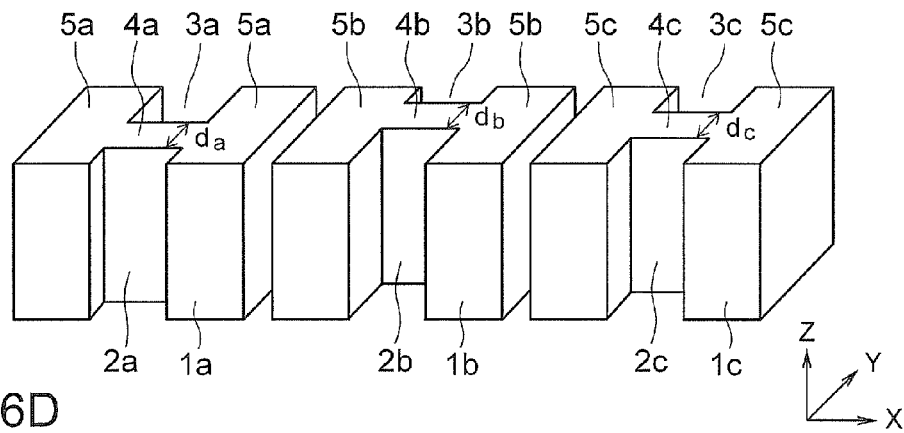

FIGS. 6B and 6C are perspective views showing the samples 1a to 1c after the slices 4a to 4c are formed. In this method, the first openings 2a to 2c and the second openings 3a to 3c are respectively formed in the samples 1a to is to form the slices 4a to 4c. Reference characters 5a to 5c designate frame portions remaining on both ends of the slices 4a to 4c, the first openings 2a to 2c, and the second openings 3a to 3c after the slices 4a to 4c are completed.

Figure 6D:
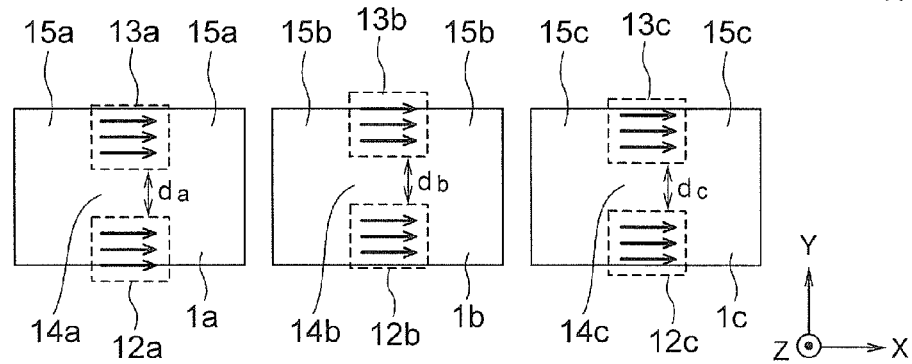

FIG. 6D is a top view showing a method for forming the slices 4a to 4c. This method forms the samples 1a to is of FIG. 6B or 6C from the samples 1a to 1c of FIG. 6A.

First, first processing boxes 12a to 12c are set on one side of slice formation scheduled regions 14a to 14c of the samples 1a to 1c, and second processing boxes 13a to 13c are set on the other side of the slice formation scheduled regions 14a to 14c of the samples is to 1c, respectively. Reference characters 15a to 15c designate frame formation scheduled regions of the samples is to 1c, respectively.

Next, regions within the first and second processing boxes 12a to 13c are scanned by a focused ion beam and are sputter-etched to form the first and second openings 2a to 3c. As a result, the slices 4a to 4c are formed in the slice formation scheduled regions 14a to 14c. In the frame formation scheduled regions 15a to 15c, frame portions 5a to 5c are made to remain.

Hereinafter, a detailed description is given of the sample processing method of FIG. 6D with reference to FIGS. 7A to 7C.

Figure 7A:
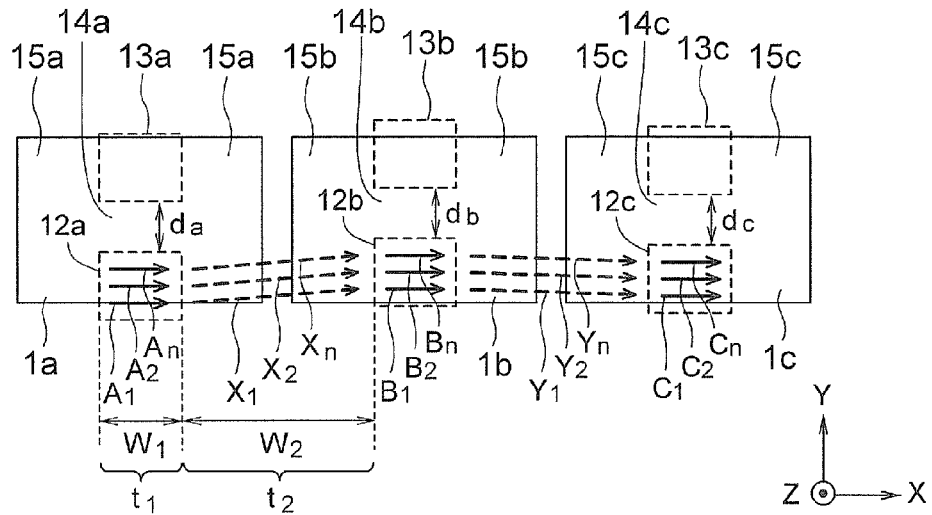
FIGS. 7A to 7C are top views for explaining the sample processing method of the second embodiment in detail.
Figure 7B:
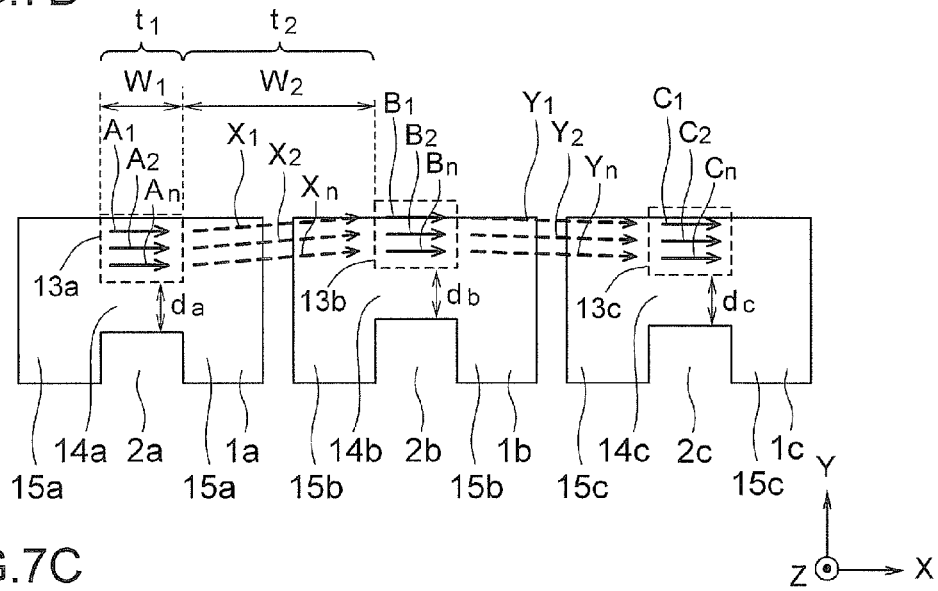
Figure 7C:
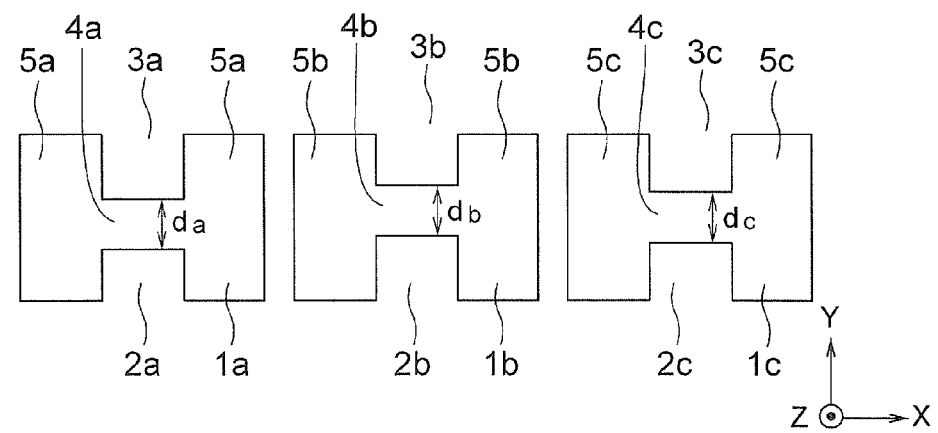

FIGS. 7A to 7C are top views for explaining the sample processing method of the second embodiment in detail.

First, as shown in FIG. 7A, primary scans are performed a plurality of times, where each primary scan sequentially scans the first processing boxes 12a to 12c of the samples 1a to 1c with a continuously generated focused ion beam. As a result, the first openings 2a to 2c are formed in the samples is to 1c (FIG. 7B).

Next, as shown in FIG. 7B, secondary scans are performed a plurality of times, each secondary scan sequentially scans the second processing boxes 13a to 13c of the samples 1a to 1c with a continuously generated focused ion beam. As a result, the second openings 3a to 3c are formed in the samples 1a to is (FIG. 7C).

In this way, the slices 4a to 4c are formed on the samples is to 1c as shown in FIG. 7C.

Each primary scan of the present embodiment is performed so that the first processing boxes 12a to 12c are sequentially scanned with a continuously generated ion beam as in the first embodiment. Similarly, each secondary scan of the present embodiment is performed so that the second processing boxes 13a to 13c are sequentially scanned with a continuously generated ion beam.

Therefore, according to the present embodiment, it is possible to suppress occurrence of variations in thicknesses of the slices 4a to 4c as in the first embodiment.

Moreover, in the present embodiment, the first scanning condition for scanning the first regions within the first and second processing boxes 12a to 13c are made different from the second scanning condition for scanning the second regions between the first processing boxes 12a to 12c and the second processing boxes 13a to 13c, to allow the frame portions 5a to 5c to remain in the regions after the slices 4a to 4c are formed as in the first embodiment.

Therefore, according to the present embodiment, it is possible to suppress occurrence of variations in thicknesses of the slices 4a to 4c while reinforcing the strength of the slices 4a to 4c with the presence of the frame portions 5a to 5c on both the sides of the slices 4a to 4c as in the first embodiment.

Third Embodiment

FIGS. 8A to 8D are perspective views and a top view for explaining a sample processing method of a third embodiment.

Figure 8A:
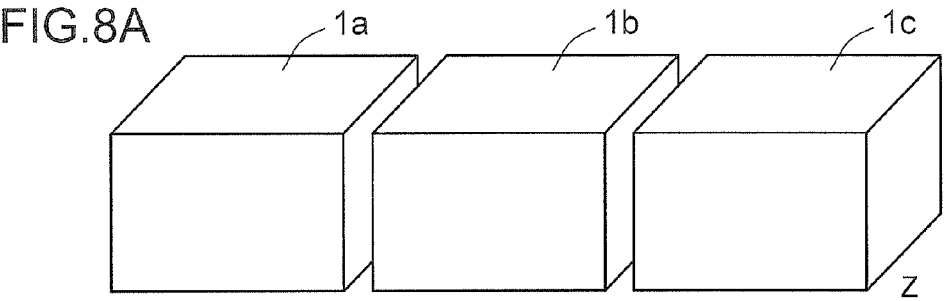
FIGS. 8A to 8D are perspective views and a top view for explaining a sample processing method of a third embodiment.
Figure 8B:
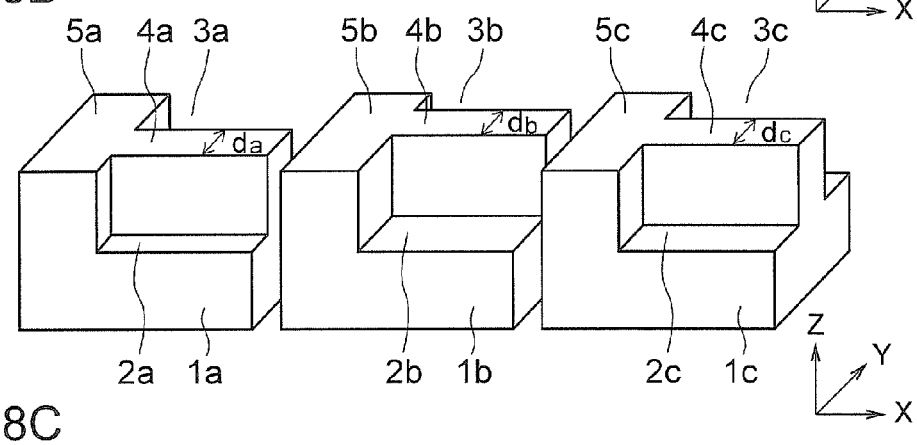
Figure 8C:
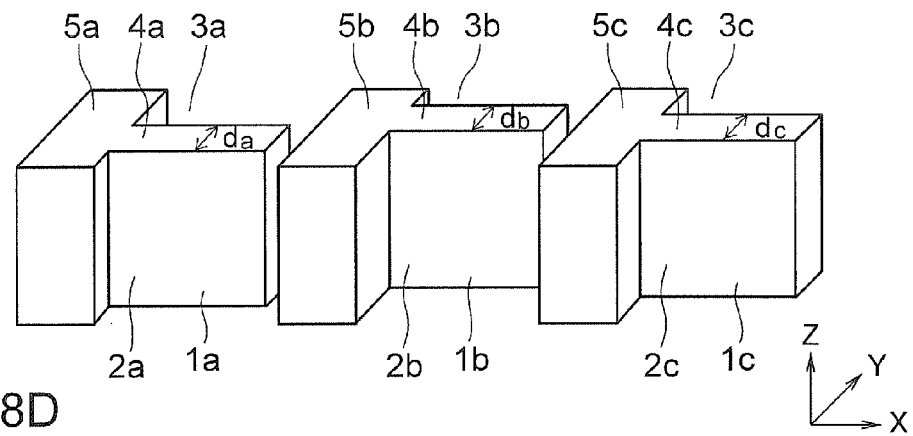
Figure 8D:
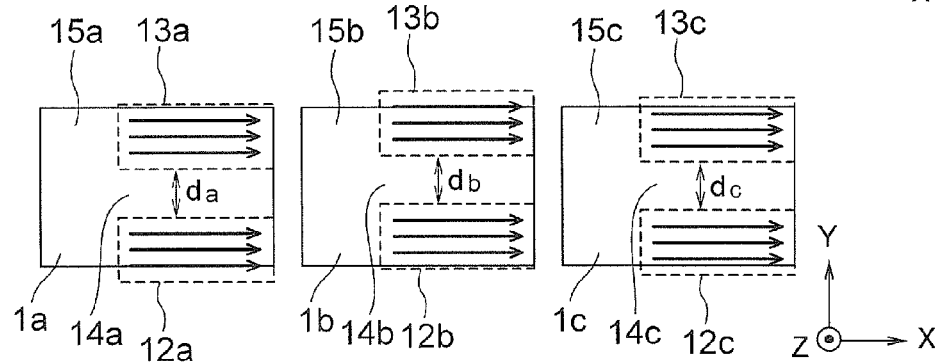

In the present embodiment, as shown in FIGS. 8B and 8C, the frame portions 5a to 5c are left on one side of the slices 4a to 4c, the first openings 2a to 2c, and the second openings 3a to 3c. The structure of the present embodiment is employed when, for example, the strength of the slices 4a to 4c can sufficiently be reinforced only with the frame portions 5a to 5c on one side of the slices 4a to 4c.

Figure 9A:
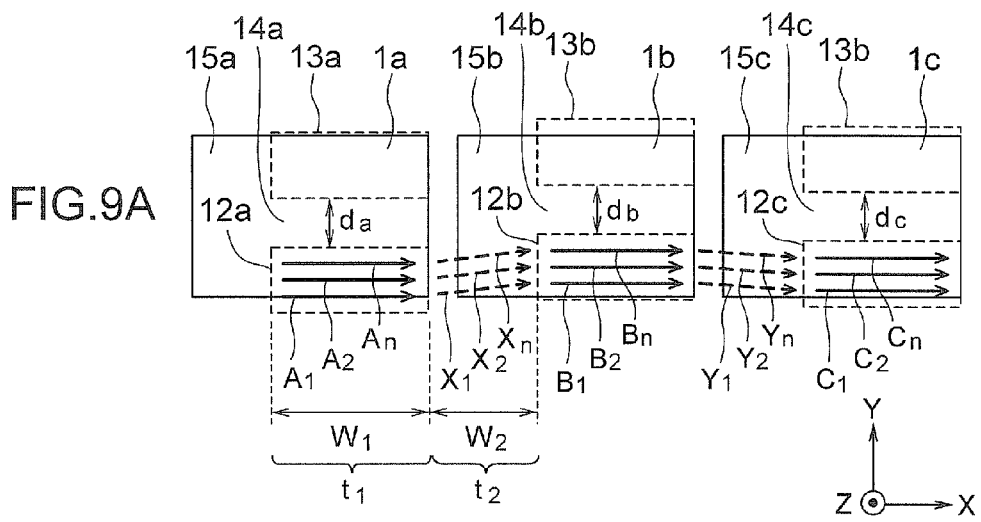
FIGS. 9A to 9C are top views for explaining the sample processing method of the third embodiment in detail.
Figure 9B:
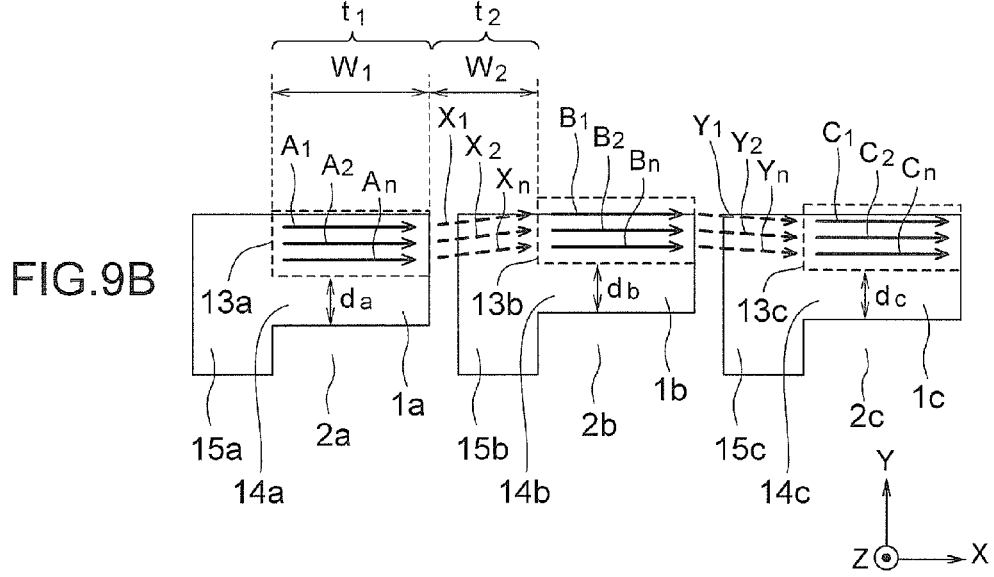
Figure 9C:
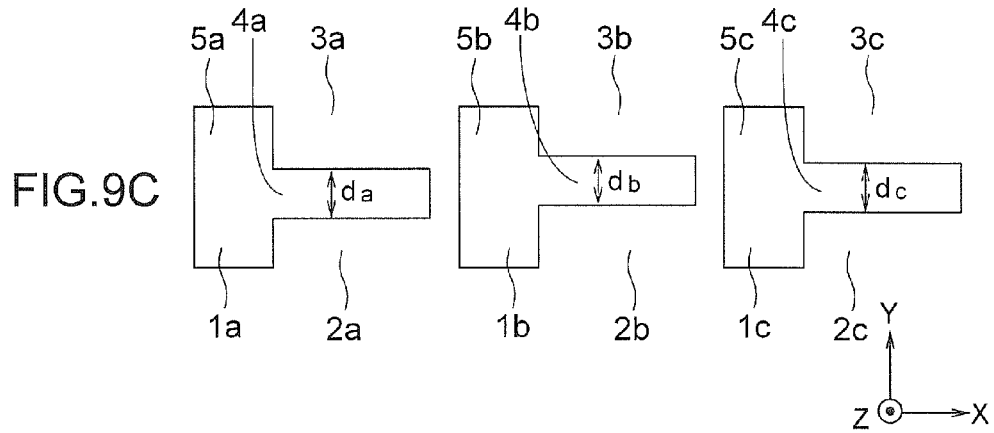

FIGS. 9A to 9C are top views for explaining the sample processing method of the third embodiment in detail.

In the present embodiment, the first scanning condition for scanning the first regions within the first and second processing boxes 12a to 13c are made different from the second scanning condition for scanning the second regions between the first processing boxes 12a to 12c and between the second processing boxes 13a to 13c, to allow the frame portions 5a to 5c to remain in the second regions between the first and second processing boxes 12a to 13c after the slices 4a to 4c are formed as in the first and second embodiments.

Therefore, according to the present embodiment, it is possible to suppress occurrence of variations in thicknesses of the slices 4a to 4c while reinforcing the strength of the slices 4a to 4c with the presence of the frame portions 5a to 5c on one side of the slices 4a to 4c as in the first and second embodiments.

While certain embodiments have been described, these embodiments have been presented by way of example only, and are not intended to limit the scope of the inventions. Indeed, the novel methods described herein may be embodied in a variety of other forms; furthermore, various omissions, substitutions and changes in the form of the methods described herein may be made without departing from the spirit of the inventions. The accompanying claims and their equivalents are intended to cover such forms or modifications as would fall within the scope and spirit of the inventions.

The invention claimed is:

1. A sample processing method comprising:
placing a sample on a sample placing module;
setting first processing boxes on one side of slice formation scheduled regions of the sample, and setting second processing boxes on the other side of the slice formation scheduled regions of the sample; and
processing the sample by performing a primary scan which sequentially scans the first processing boxes with a continuously generated ion beam, and a secondary scan which sequentially scans the second processing boxes with a continuously generated ion beam, to form a plurality of slices of the sample,
wherein the primary and secondary scans are performed so that a first scanning condition for scanning first regions within the first and second processing boxes is set different from a second scanning condition for scanning second regions between the first processing boxes and between the second processing boxes, to allow frame portions of the sample to remain in the second regions after the slices are formed.

2. The method of claim 1, wherein the primary and secondary scans are performed so that second dwell time for scanning each second region is set shorter than first dwell time for scanning each first region.

3. The method of claim 1, wherein the primary and secondary scans are performed so that a second scanning speed for scanning each second region is set faster than a first scanning speed for scanning each first region.

4. The method of claim 1, wherein the slices are formed so that a height of the frame portions becomes equal to or larger than half of a height of the slices.

5. The method of claim 1, wherein the slices are formed by performing the primary scans a plurality of times and performing the secondary scans a plurality of times, each primary scan sequentially scanning the first processing boxes once, and each secondary scan sequentially scanning the second processing boxes once.

6. The method of claim 5, wherein the secondary scans are started after the primary scans are finished.

7. The method of claim 5, wherein the primary and secondary scans are performed alternately.

8. The method of claim 5, wherein the primary and secondary scans include a first-directional scan which proceeds in a first direction, and a second-directional scan which proceeds in a second direction which is opposite to the first direction.

9. The method of claim 5, wherein the primary and secondary scans include a first-directional scan which proceeds in a first direction, and do not include a second-directional scan which proceeds in a second direction which is opposite to the first direction.

10. The method of claim 5, wherein the primary and secondary scans are performed so that intensity of the ion beam is unchanged during performing a primary or secondary scan once.

11. A sample processing method comprising:
placing samples on a sample placing module;
setting a first processing box on one side of a slice formation scheduled region of each sample, and setting a second processing box on the other side of the slice formation scheduled region of each sample; and
processing the samples by performing a primary scan which sequentially scans the first processing boxes of the samples with a continuously generated ion beam, and a secondary scan which sequentially scans the second processing boxes of the samples with a continuously generated ion beam, to form a plurality of slices of the samples,
wherein the primary and secondary scans are performed so that a first scanning condition for scanning first regions within the first and second processing boxes is set different from a second scanning condition for scanning second regions between the first processing boxes and between the second processing boxes, to allow at least one frame portion of each sample to remain in the second regions after the slices are formed.

12. The method of claim 11, wherein the primary and secondary scans are performed so that second dwell time for scanning each second region is set shorter than first dwell time for scanning each first region.

13. The method of claim 11, wherein the primary and secondary scans are performed so that a second scanning speed for scanning each second region is set faster than a first scanning speed for scanning each first region.

14. The method of claim 11, wherein the slices are formed so that a height of the frame portions of the samples becomes equal to or larger than half of a height of the slices.

15. The method of claim 11, wherein the slices are formed by performing the primary scans a plurality of times and performing the secondary scans a plurality of times, each primary scan sequentially scanning the first processing boxes of the samples once, and each secondary scan sequentially scanning the second processing boxes of the samples once.

16. The method of claim 15, wherein each the secondary scans are started after the primary scans are finished.

17. The method of claim 15, wherein the primary and secondary scans are performed alternately.

18. The method of claim 15, wherein the primary and secondary scans include a first-directional scan which proceeds in a first direction, and a second-directional scan which proceeds in a second direction which is opposite to the first direction.

19. The method of claim 15, wherein the primary and secondary scans include a first-directional scan which proceeds in a first direction, and do not include a second-directional scan which proceeds in a second direction which is opposite to the first direction.

20. The method of claim 15, wherein the primary and secondary scans are performed so that intensity of the ion beam is unchanged during performing a primary or secondary scan once.

* * * * *